United States Patent [19]
Schad

[11] Patent Number: 5,676,678
[45] Date of Patent: Oct. 14, 1997

[54] SURGICAL INSTRUMENT WITH RELEASABLE JAW HOLDER

[76] Inventor: Gerhard Schad, Haldenstrasse 13/1, D-78600 Kolbingen, Germany

[21] Appl. No.: 583,113

[22] PCT Filed: Jun. 1, 1994

[86] PCT No.: PCT/EP94/01777

§ 371 Date: Jan. 16, 1996

§ 102(e) Date: Jan. 16, 1996

[87] PCT Pub. No.: WO95/02365

PCT Pub. Date: Jan. 26, 1995

[30] Foreign Application Priority Data

Jul. 17, 1993 [DE] Germany .................. 43 24 042.9

[51] Int. Cl.$^6$ .................................................. A61B 17/34
[52] U.S. Cl. .................................. 606/170; 606/207
[58] Field of Search .............................. 606/206–207, 606/159–160, 167, 170, 174, 180, 198; 604/104–105, 22; 128/751; 30/237, 253

[56] References Cited

U.S. PATENT DOCUMENTS

| | | | |
|---|---|---|---|
| 4,177,814 | 12/1979 | Knepshield et al. | 606/170 X |
| 4,273,128 | 6/1981 | Lary | 606/170 X |
| 4,509,517 | 4/1985 | Zibelin | 606/170 X |
| 4,655,219 | 4/1987 | Petruzzi | 606/170 X |
| 4,848,338 | 7/1989 | De Satnick et al. | 606/170 X |
| 5,254,130 | 10/1993 | Poncet et al. | 606/206 |
| 5,366,466 | 11/1994 | Christian et al. | 606/174 |
| 5,383,895 | 1/1995 | Holmes et al. | 606/206 |
| 5,433,725 | 7/1995 | Christian et al. | 606/207 |
| 5,509,923 | 4/1996 | Middleman et al. | 606/207 |

FOREIGN PATENT DOCUMENTS

| | | |
|---|---|---|
| 0 225 045 | 6/1987 | European Pat. Off. |
| 0 541 930 A1 | 5/1993 | European Pat. Off. |
| 0 546 767 A2 | 6/1993 | European Pat. Off. |
| 0 609 503 A1 | 8/1994 | European Pat. Off. |
| 91 05 399.4 | 9/1991 | Germany |
| 91 14 306.3 | 2/1992 | Germany |
| WO91/02493 | 3/1991 | WIPO |

*Primary Examiner*—Michael Buiz
*Assistant Examiner*—Nancy Connolly Mulcare
*Attorney, Agent, or Firm*—Barry R. Lipsitz; Ralph F. Hoppin

[57] ABSTRACT

In a surgical instrument with at least one jaw part (9) actuatable via a pull or push element (10), the pull or push element (10) is to extend through a tube (13), at the end of which the at least one jaw part (9) is arranged. The jaw part (9) is releasably connected to the tube (13) via a holder (8) and is arranged for removal together with the pull or push element (10) from the tube (13).

19 Claims, 4 Drawing Sheets

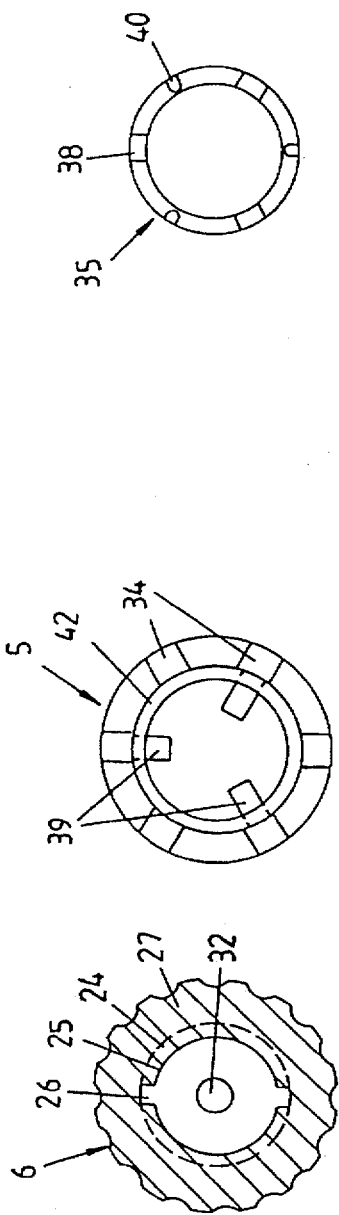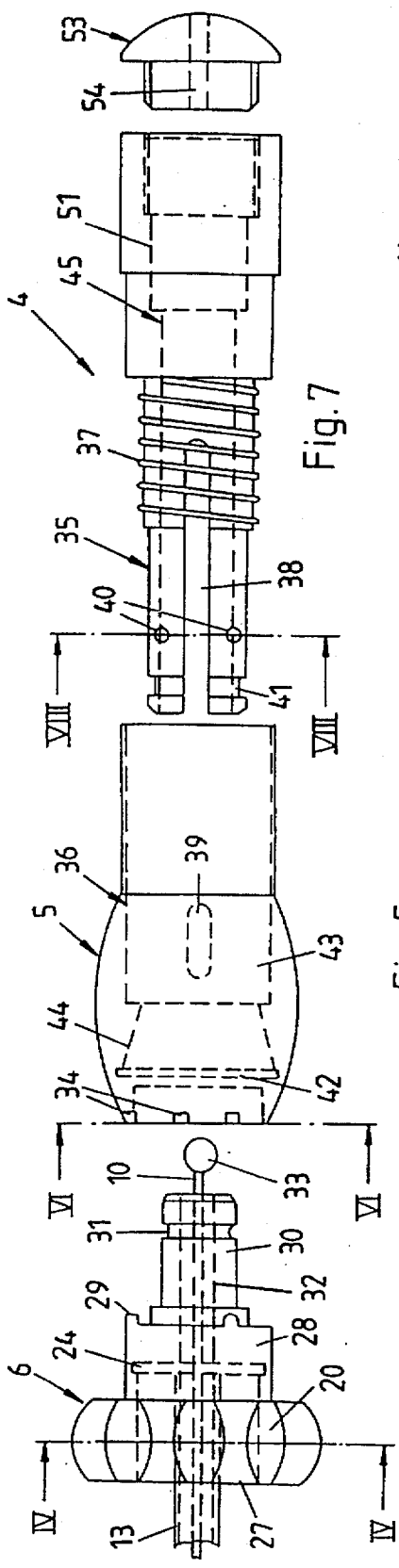

5,676,678

SURGICAL INSTRUMENT WITH RELEASABLE JAW HOLDER

BACKGROUND OF THE INVENTION

The invention relates to a surgical instrument with at least one jaw part actuatable via a pull or push element. The pull or push element extends through a tube having the at least one jaw part releasably connected to the end thereof, and being surrounded by an outer tube which is slideably seated on the tube.

Tong-like surgical instruments are known in various shapes and designs. These are grasping instruments, biopsy instruments, cutting instruments, needle and thread holders, grasping forceps, dissection forceps, spoon-type forceps, etc. All these instruments have in common that jaw parts are actuated by an actuating device. The jaw parts can be scissors, forceps, cutters, clamps or the like. In most cases, two jaw parts are moveable, but arrangement of only one jaw part which is moveable in relation to a fixed jaw part is also conceivable.

As a rule, these jaw parts are actuated via a pull or push element. The pull element consists, for example, of a wire cord, a pull or push element comprised of wire sections, rods, tubes or the like.

These pull or push elements and simultaneously the corresponding jaw parts are actuated manually via scissor handles or electrically via motors, pneumatically, hydraulically or in a similar way. Here many designs are possible and are to be covered by the present invention.

SUMMARY OF THE INVENTION

All of these aforementioned surgical instruments have to perform very different functions during handling on or in the human body and should, therefore, be designed for as wide a variety of applications as possible. Nowadays, however, in spite of the varied design, it is essential for the surgical instrument to be easy to disassemble into individual parts and to clean. Today, the very high demands made on hygiene and sterilization are unable to be met by the current surgical instruments. Either they are of very complicated design and can, therefore, perform very different functions, but, in turn, are difficult to disassemble and reassemble. Or, they are of simple construction and can be taken apart, but, as a rule, only fulfill a single function and are difficult to handle.

Surgical instruments of this kind are described in EP 0 546 767A2. Herein the actual tong- or scissor-shaped tools are rotatably mounted on a holder which is permanently fixed in a tube shaft of the instrument, for example, by crimping the tube shaft. With this instrument, the holders with the tools mounted thereon are not exchangeable and so the entire instrument has to be exchanged when changing over to another instrument. Disassembly for cleaning purposes is difficult.

Such tong-shaped instruments are described in WO91/02493. Herein the tools are releasably mounted on a tube shaft. However, insertion of the tools is difficult because the tools are held on a bearing shaft and have to be fitted with a toothing in toothed racks which are displaceably mounted on the instrument itself. It is, therefore, extremely difficult to exchange these tools.

Departing from this prior art, the object underlying the invention is to so design a surgical instrument of the generic kind for a variety of applications that, on the one hand, it can be very thoroughly cleaned or sterilized and, on the other hand, the tool can be exchanged in a simple way.

This object is accomplished in accordance with the invention in a surgical instrument of the kind described at the outset in accordance with a first preferred embodiment in that the jaw part is connected to a holder in the fashion of a rotary joint, in that the holder is releasably coupled with the tube, and in that the holder has a projection which in the operational position is seated in a cavity of the tube and is held by snap legs of the tube.

This object is accomplished in accordance with the invention in a surgical instrument of the kind described at the outset in accordance with a second preferred embodiment in that the jaw part is connected to a holder in the fashion of a rotary joint, in that the holder is releasably coupled with the tube, and in that the tube is designed in the fashion of a collet at the end thereof, and the collet Grippers embrace a part formed on the holder.

With this design of the surgical instrument, above all, exchange of a Great number of different jaw parts is possible, and, therefore, a multiplicity of surgical operations can be performed with the basic instrument. Herein elements can also be easily separated from one another and cleaned. This applies, above all, to the tube core and the pull element. What is essential herein is that the holder is of the same design for all jaw parts. In accordance with the function of the jaw parts, these are also connected to the holder, as a rule, via a rotary joint, and coupled with the pull element. A great number of possibilities for actuating jaw parts are known and are to be covered by the present invention.

The pull element and the holder can be separated, together with the jaw parts, from the tube. The tube and the unit comprised of pull element, holder and jaw part are then cleaned or sterilized separately. If requested, a number of different jaw parts with holder and pull or push element can now be offered with a basic instrument. These different jaw parts are exchanged according to requirements.

A closure is provided to fix the holder on the tube. It consists of an outer tube which surrounds the inner tube. When the outer tube is displaced, it also engages over the cavity and the projection of the holder seated in the cavity and the snap legs or the collet grippers so these cannot be spread apart. The holder is fixed in this way on the inner tube.

In a preferred embodiment, the inner tube is seated in a rotary part and is releasably connected via this rotary part to other parts of a surgical instrument, with not only the rotary part but also the pull element being releasable from the other part. This rotary part may, but does not have to, also serve to rotate the jaw part. In a certain position, it can also be firmly connected to the other instrument parts and, therefore, this embodiment is also to be covered by the present invention.

The rotary part preferably comprises a recess which surrounds the inner tube and in which an end piece of the outer tube is also arranged and supported via a spring, preferably a helical spring. The end piece is fixed in the recess in the fashion of a bayonet closure. For this purpose, hook projections on the end piece are guided in an annular groove in the recess. During rotation of the end piece, these hook projections can be brought to a first rim edge, at which the outer tube engages over the cavity and the projection as well as the snap legs. When the end piece is rotated further, the hook projections arrive in the region of longitudinal slots so the outer tube can be separated from the rotary part. In this way, outer tube and inner tube can be cleaned separately. This design also enables arrangement of very different seals, sealing rings, etc. which prevent impurities from passing rearwardly through the rotary part, the space between outer tube and inner tube, and the inner tube into the other parts of the surgical instrument.

In the preferred embodiment, the rotary part is, as the name indicates, rotatably arranged so the jaw parts can assume a different position. The rotation can be through 360 degrees. Rotation is delimited by detent noses which engage in detent depressions of a thrust part. This thrust part is, in turn, releasably seated on a clamping part which serves to releasably hold the rotary part. For this purpose, the thrust part engages over a tube section of the clamping part in which the rotary part is inserted with a bolt section. This bolt section has an annular channel into which balls are pressed by means of the thrust part. This is done via a conical bore in the thrust part. The balls sit in corresponding ball receptacles in the tube section.

The thrust part is also releasably connected to the clamping part. This is done by a snap ring which can be inserted into an annular groove of the tube section and in the operational position engages behind a stop ring within the thrust part. Furthermore, the thrust part is supported via a spring, preferably a helical spring, on the clamping part, and is pressed via this helical spring against the rotary part so the detent depressions receive the aforementioned detent noses.

An insert which connects the pull or push element with an actuating device is, in turn, slideably arranged in the clamping part. For this purpose, the insert consists of a collet part with a cavity for receiving a ball formed on the pull or push element. The collet legs of the collet part or a corresponding collet head is subjected to the pressure of guide cams which act from the thrust part through longitudinal slots in the tube section of the clamping part on the collet legs. When the thrust part is displaced, the pressure of the guide cams on the collet head decreases, as this collet head is followed by an annular hollow. By means of a simple pull, the ball slides out of the ball cavity and so the pull element is released from the insert.

A connecting rod for an actuating device is slideably mounted in the insert. The opening width of the jaw parts can be determined by displacement and subsequent fixing of this connecting rod.

In the present embodiment, the connecting rod is then adjoined by a ball which is detachably connected to a handle part. In this embodiment, the actuating device consists for reasons of simplicity of two handle parts, but all other aforementioned actuating devices are also conceivable.

The insert is, in turn, actuated against the pressure of a spring which is supported between the collet part and a cover. The cover, through which the connecting rod extends, closes the clamping part.

In all, this design provides a surgical instrument which offers an extremely large range of possible uses, is very flexible to handle, is extremely easy to take apart and clean. Its assembly also poses no problems, and, above all, the exchangeability of the jaw parts is to be emphasized.

Further advantages, features and details of the invention are to be found in the following description of preferred embodiments and in the drawings, which show in

BRIEF DESCRIPTION OF THE DRAWINGS

FIG. 3 a plan view of a rotary part for the surgical instrument according to FIG. 1;

FIG. 4 a cross section through the rotary part according to FIG. 3 along line IV—IV;

FIG. 5 a plan view of a thrust part for the surgical instrument according to FIG. 1;

FIG. 6 an end view of the thrust part according to FIG. 5 along line VI—VI;

FIG. 7 a plan view of a clamping part for the surgical instrument according to FIG. 1;

FIG. 8 a cross section through the clamping part according to FIG. 7 along line VIII—VIII;

FIG. 9 a plan view of an insert in the clamping part according to FIG. 7;

DETAILED DESCRIPTION OF THE INVENTION

Figure 1:
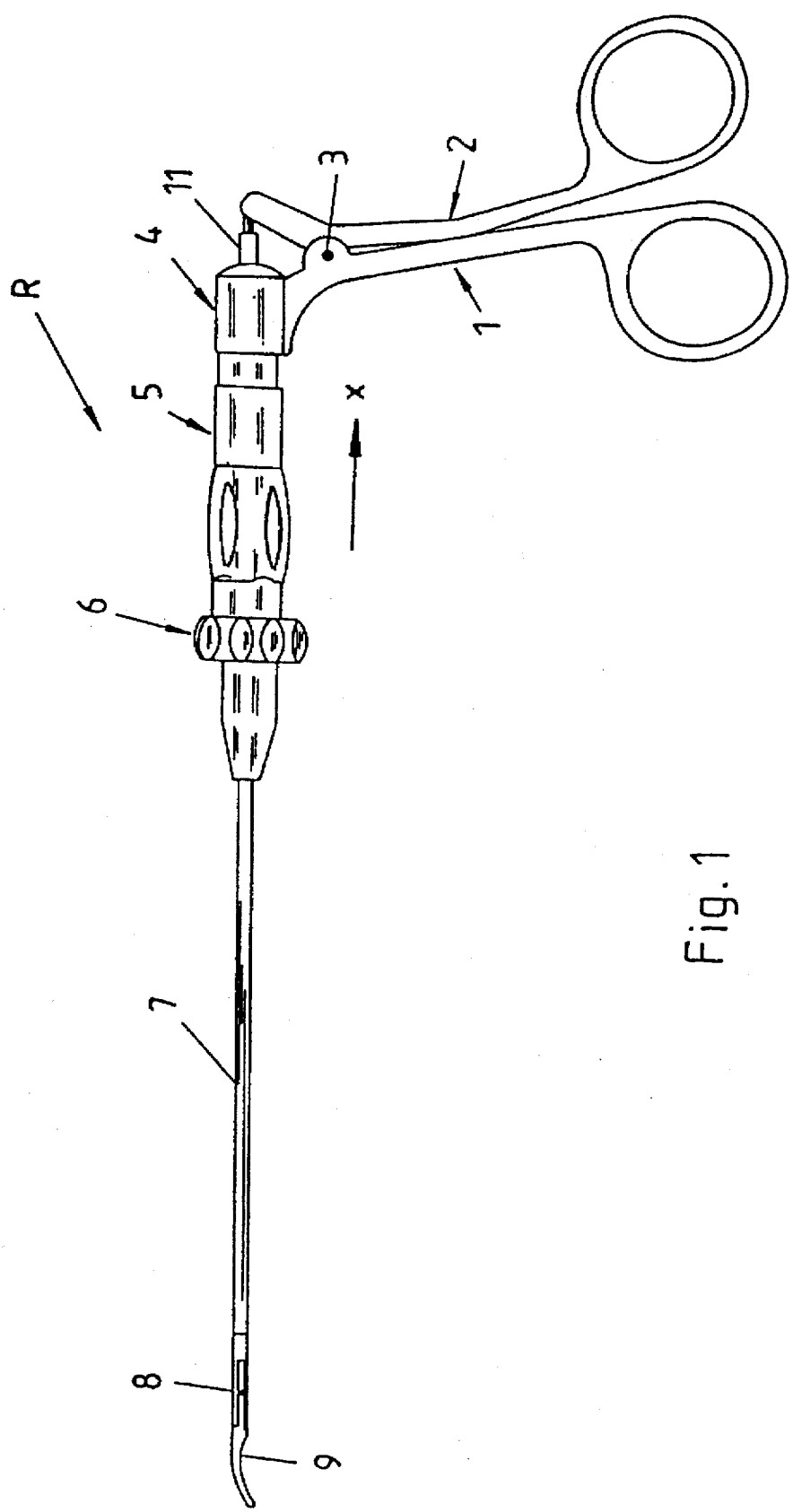
FIG. 1 a plan view of a surgical instrument according to the invention.

In accordance with FIG. 1, a surgical instrument R comprises two handle parts 1 and 2 which are joined to one another via a rotary joint 3. The handle part 1 is firmly connected to a clamping part 4 on which a thrust part 5 slideable in direction x is partly seated. A rotary part 6 adjoins the thrust part 5. An outer tube 7 leads from the rotary part 6 to a holder 8 for jaw parts 9 which can be of any chosen design. The jaw parts 9 are connected via a pull element 10 shown in FIG. 3 to an insert 11 which, in turn, is articulatedly connected to the handle part 2.

Figure 2:
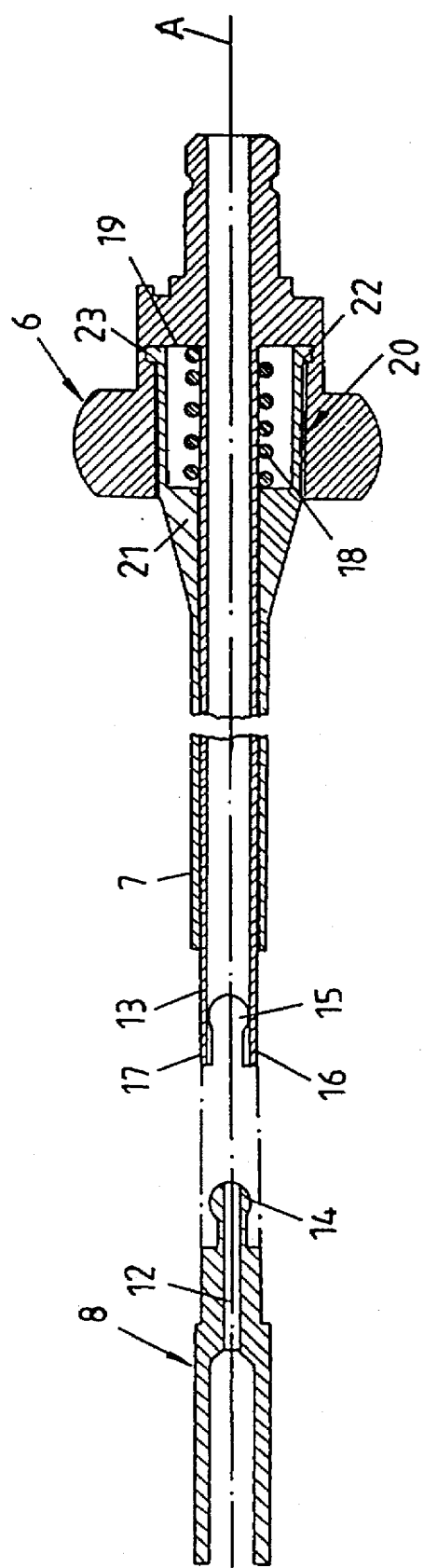
FIG. 2 a longitudinal section through parts of the surgical instrument according to FIG. 1, partly in exploded representation.

From FIG. 2 it is apparent that the holder 8 is of fork-shaped design. However, this is only one embodiment. All possible holders, all possible jaw parts and all possible rotary joint-type connections between the jaw parts and the holder and between the jaw parts and the pull element 10 are to be covered by the present invention. These include, for example, known grasping forceps, forceps for sample excision, biopsy forceps, tissue forceps, needle holders, scissors, dissection forceps, etc. Reference is made, only by way of example, to biopsy forceps according to European patent application 0 065 054 and French patent 2 479 608 or to a surgical instrument according to European patent application 0 119 405. All of these surgical instruments operate with jaw parts which carry out a cutting, clamping, shearing or similar operation and are actuated by a pull element.

In the present embodiment, the pull element 10 is in the form of a wire, but it could also be a cord or a tube. For linkage to the jaw parts, not shown in further detail in FIG. 2, the pull element 10 extends through an inner bore 12 within the holder 8.

A releasable coupling of the holder 8 with the other parts of the surgical instrument R is an essential feature of the present invention. In the present embodiment, the holder comprises for detachable coupling with an inner tube 13 a projection 14 through which the inner bore 12 likewise extends. This projection 14 can be pushed into a corresponding cavity 15 in the inner tube 13 and two snap legs 16 and 17 engage over the projection 14 to fix it. The snap legs 16 and 17 are of resilient design so the holder 8 can be pulled out of the cavity 15 when the snap legs 16 and 17 expand elastically.

The projection 14 is fixed in the cavity 15 by the outer tube 7. This outer tube 7 is seated, and the inner tube 13 as well, in the rotary part 6. However, whereas the inner tube 13 is fixed in the rotary part 6, the outer tube 7 is supported on a bottom 19 of a recess 20 in the rotary part 6 via a helical spring 18 which surrounds the inner tube 13.

In the operational position shown in FIG. 2, in which the cavity 15 is free and in which the holder 8 can be separated from the inner tube 13, an end piece 21 of the outer tube 7 is fully located within the recess 20 against the pressure of the helical spring 18 and with hook projections 22 engages behind undercut rim edges 23 therein.

By rotating the end piece 21, the hook projections 22 are also rotated in a corresponding annular groove 24 shown in FIGS. 3 and 4 and arrive at a second undercut rim edge 25 which is further away from the bottom 19. The helical spring 18 then presses the hook projections 22 against this rim edge 25, and the outer tube 7 is displaced towards the holder 8 in the direction opposite to thrust direction x and thereby engages over the cavity 15 and the snap legs 16 and 17. This engaging over the snap legs 16 and 17 prevents them from expanding, and the projection is, therefore, held firmly in the cavity 15.

The end piece 21 can execute yet a further rotation so the hook projections 22 arrive in regions of longitudinal slots 26 (see FIG. 4), and the end piece 21 and hence the outer tube 7 can be released from the rotary part 6. This enables better cleaning of the core of the outer tube 7 and the recess 20.

A further feature of the present invention is that the inner tube 13 and hence also the holder 8 and the law parts 9 are arranged by means of the rotary part 6 for rotation about a longitudinal axis A. For this purpose, as mentioned hereinabove, the inner tube 13 is fixed in the rotary part 6. The rotary part 6 comprises a rotary ring 27 with corresponding knurls, which is adjoined by an annular part 28 with detent noses 29. The annular part 28 is followed by a bolt section 30 of smaller diameter with an annular channel 31.

Together with the annular groove 24, the recess 20 engages at least partly in the annular part 28. Adjoining this in the annular part 28 and the bolt section 30 is an axial bore 32, through which the pull element 10 extends. A ball 33 is then placed on the end of the pull element 10.

In the operational position, the bolt section 30 engages in the thrust part 5 in accordance with FIG. 5, and the detent noses 29 are received in detent depressions 34. When the thrust part 5 is displaced somewhat in direction x, the detent noses 29 are released, and the rotary part 6 can be rotated about the longitudinal axis A.

The thrust part 5 is pushed onto the clamping part 4 in accordance with FIG. 7, and this clamping part 4 engages with a tube section 35 in a stepped bore 36 of the thrust part 5. The thrust part 5 is then supported in relation to the clamping part 4 via a helical spring 37 which encircles the tube section 35. The helical spring 37 presses the thrust part 5 in the direction opposite to thrust direction x.

In the present embodiment, three longitudinal slots 38 are formed in the tube section 35, and in the operational position guide cams 39 inserted in the thrust part 5 engage these longitudinal slots. These guide cams 39 have a further function relating to the insert 11, which will be described hereinbelow.

Also formed in the tube section 35 are ball receptacles 40 and an annular groove 41. The annular groove 41 serves to receive a snap ring, not shown in further detail, which is inserted in the annular groove 41 after insertion of the clamping part 4.

The snap ring then engages behind a stop ring 42 (see FIG. 6), which protrudes into the inside diameter of the stepped bore 36 of the thrust part 5. The snap ring thus prevents the thrust part 5 from being released from the clamping part 4.

Between a receiving chamber 43 of the stepped bore 36 for the helical spring 37 and the stop ring 42, the stepped bore 36 is designed as a conical bore 44. This conical bore 44 cooperates with balls, not shown in further detail, in the ball receptacles 40. When the thrust part 5 is pushed in the direction opposite to thrust direction x, the conical bore 44 presses the balls into the ball receptacles 40, and, on the other hand, the balls are pressed into the annular channel 31 of the bolt section 30 of the rotary part 6. The rotary part 6 is thereby releasably connected to the clamping part 4.

A stepped bore also extends through the clamping part 4. Seated in this stepped bore 45 in accordance with FIG. 9 is the insert 11. This insert 11 consists of a collet part 46 and a connecting rod 47 which is displaceably seated in a longitudinal bore 48 of the collet part 46. The connecting rod 47 is fixed in the longitudinal bore 48 by a headless screw 49. The headless screw 49 extends through a flange 50 which in the operational position can slide in an inner chamber 51 of the stepped bore 45 of the clamping part 4. The sliding occurs against the pressure of a helical spring 52 which is supported, on the one hand, on the flange 50, and, on the other hand, on a cover 53 screwed into the stepped bore 45. The connecting rod 47 extends through a bore 54 in the cover 53 and at the end is seated in the operational position with a ball 55 in a ball receptacle of the handle part 2.

The collet part 46 serves to fix the pull element 10, and the ball 33 is then received in a ball cavity 56. For this purpose, collet legs 58 which can expand elastically are formed by slots 57 in the collet part 46. However, such expansion is prevented by the guide cams 39 so long as the thrust part 5 rests against the annular part 28 of the rotary part 6. In this operational position, the guide cams 39 press on a collet head 59 so the collet legs 58 remain in the closed position.

However, when the thrust part 5 is displaced in thrust direction x on the clamping part 4, the guide cams 39 slide into an annular hollow 60 of the collet part 46 and release the collet legs 58 to a limited extent. These can then expand elastically so the ball 33 can slide out of the ball cavity 56.

Figure 10:
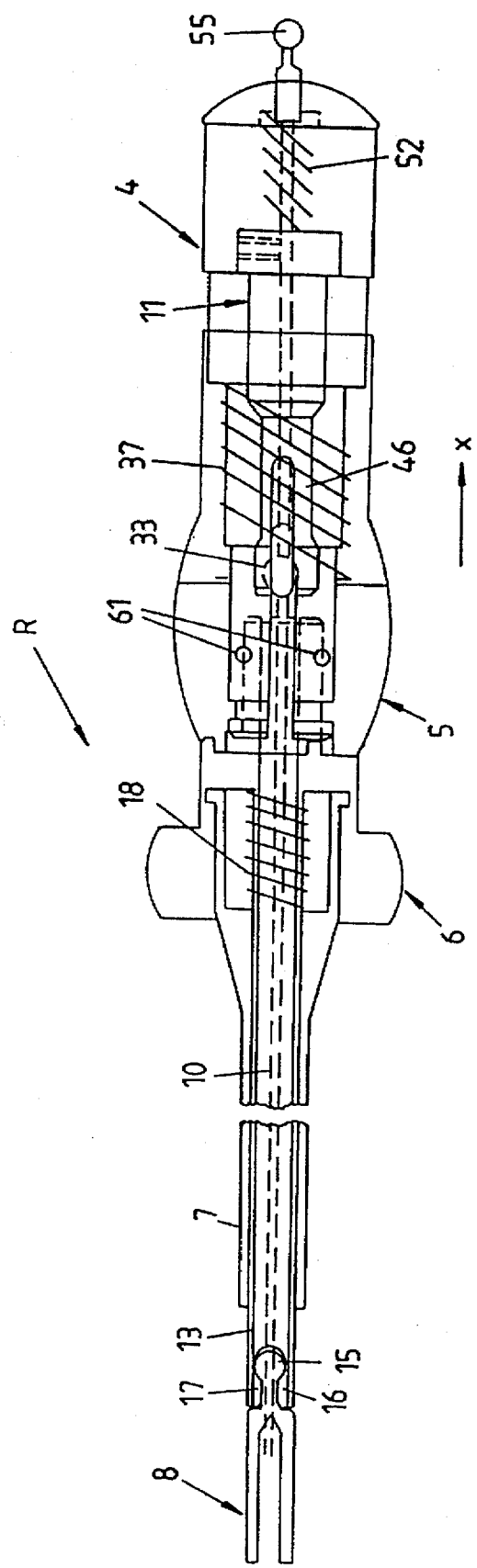
FIG. 10 a plan view illustrating operation of the surgical instrument according to FIG. 1.

The operating principle of the present invention is shown diagrammatically in FIG. 10. Via the ball 55 of the insert 11, the pull element 10 and hence the jaw parts 9, not shown in further detail, are connected to the handle part 2, likewise not shown in further detail, which is in articulated connection with the other handle part 1 via the rotary joint 3. By actuating handle parts 1 and 2, the insert 11 is moved against the pressure of the helical spring 52, taking the pull element 10 along with it, and thereby actuating the jaw parts 9. As the pull element 10 with its ball 33 is held movably by the collet part 46, the pull element 10 can readily rotate about the longitudinal axis A and so the position of the jaw parts 9 is changeable. This is done by rotating the rotary part 6, with the thrust part 5 being displaced slightly in direction x so the detent noses 29 are free. If the thrust part 5 is then released, it returns to its initial position again under the pressure of the helical spring 37, and the detent noses 29 move into the detent depressions 34.

To exchange the jaw parts 9 and to clean the entire surgical instrument R, the thrust part 5 is displaced fully in direction x against the pressure of the helical spring 37. Balls 61 in the ball receptacles 40 are then released and can thus slide out of the annular channel 31 of the rotary part 6. At the same time, however, the guide cams 39 also move into the region of the annular hollow 60 and so the collet legs 58 are free and can spread apart. This enables the ball 33 to be pulled out of the corresponding ball cavity 56. The region of the rotary part 6 with outer tube and inner tube and pull element 10 is thus separated from the region with thrust part 5, clamping part 4 and insert 11.

If the pull element 10 is to be separated together with the holder 8 from the inner tube 13, the outer tube 7 is pressed into the rotary part 6 against the pressure of the helical spring 18 so the cavity 15 with the projection 14 and the snap legs 16 and 17 are released. The holder 8 can then be separated together with the pull element 10 from the inner tube 13 and replaced by other jaw parts with a corresponding holder 8 and a pull element 10.

To enable cleaning, the outer tube 7 is rotated even further so the hook projections 22 can slide through the longitudinal slots 26, and the outer tube 7 can thereby be separated from the rotary part 6.

It is self-evident that, in particular in the rotary part, appropriate sealing rings and sealing means are arranged both between inner tube 13 and outer tube 7 and between inner tube 13 and pull element 10 to prevent blood, tissue fluid or the like from travelling rearwardly through the inner tube 13 or between inner tube 13 and outer tube 7 or also through the rotary part 6 into the region of the thrust part 5.

The invention claimed is:

1. A surgical instrument with at least one jaw part actuatable via a pull or push element, said pull or push element extending through an inner tube having said at least one jaw part releasably connected to an end thereof, and being surrounded by an outer tube which is slidably seated on said inner tube, wherein:

said jaw part is connected to a holder in the fashion of a rotary joint; and an end of said holder is releasably coupled to said end of said inner tube via a projection which is releasably seated in a cavity;

said projection being secured in said cavity when said outer tube is slidably positioned to substantially surround said projection.

2. An instrument as defined in claim 1, wherein:

said cavity is disposed at said end of said inner tube;

said projection is disposed at said end of said holder.

3. An instrument as defined in claim 2, wherein:

snap legs are disposed at said end of said inner tube for releasably seating said projection of said holder in said cavity of said inner tube.

4. An instrument as defined in claim 2, wherein:

said inner tube is designed in the fashion of a collet at said end thereof, with collet grippers embracing said projection of said holder for releasably seating said projection in said cavity of said inner tube.

5. An instrument as defined in claim 1, wherein:

said pull or push element extends through an inner bore in said holder.

6. An instrument as defined in claim 1, wherein:

said inner tube is connected to a rotary part for rotation therewith.

7. An instrument as defined in claim 6, wherein:

said rotary part has a recess which surrounds said inner tube and in which said outer tube is supported against a spring and releasably guided.

8. An instrument as defined in claim 7, wherein:

said outer tube is guided with hook projections in an annular groove in said recess, said annular groove having undercut rim edges, and axially parallel longitudinal slots being formed in said recess.

9. An instrument as defined in claim 7, wherein:

said rotary part is releasably connected to a clamping part.

10. An instrument as defined in claim 9, wherein:

a thrust part is placed on a tube section of said clamping part and is supported via a spring against said clamping part.

11. An instrument as defined in claim 10, wherein the thrust part has detent depressions for receiving detent noses on said rotary part.

12. An instrument as defined in claim 10, wherein:

said thrust part acts on balls in ball receptacles in said tube section by means of a conical bore and presses these into an annular channel in a bolt section of said rotary part.

13. An instrument as defined in claim 10, wherein:

said tube section has an annular groove for insertion of a snap ring which in the operational position engages behind a stop ring in said thrust part.

14. An instrument as defined in claim 9, wherein:

an insert which releasably connects said pull or push element with an actuating device is slidably arranged in said clamping part.

15. An instrument as defined in claim 14, wherein:

said insert comprises a collet part which has a ball cavity for receiving a ball formed on said pull or push element.

16. An instrument as defined in claim 15, wherein:

a thrust part is placed on a tube section of said clamping part and is supported via a spring against said clamping part; and collet legs of said collet part are subjected to the pressure of guide cams of said thrust part.

17. An instrument as defined in claim 16, wherein:

a thrust part is placed on a tube section of said clamping part and is supported via a spring against said clamping part; and said guide cams pass through longitudinal slots in said tube section of said clamping part and act with pressure on a collet head of said collet part, and an annular hollow adjoins said collet head.

18. An instrument as defined in claim 15, wherein:

a connecting rod having a ball for connection to a handle part is releasably connected to said collet part.

19. An instrument as defined in claim 18, wherein:

said collet part is supported via a spring against a cover through which said connecting rod extends.

* * * * *